(12) United States Patent
Srinivasan et al.

(10) Patent No.: US 10,221,149 B2
(45) Date of Patent: Mar. 5, 2019

(54) PROCESS FOR THE PREPARATION OF GAMMA-VALEROLACTONE BY CATALYTIC HYDROGENATION OF LEVULINIC ACID USING RU-BASED CATALYSTS

(71) Applicant: COUNCIL OF SCIENTIFIC & INDUSTRIAL RESEARCH, New Delhi (IN)

(72) Inventors: Kannan Srinivasan, Bhavnagar (IN); Sreedhar Gundekari, Bhavnagar (IN)

( * ) Notice: Subject to any disclaimer, the term of this patent is extended or adjusted under 35 U.S.C. 154(b) by 150 days.

(21) Appl. No.: 15/518,217

(22) PCT Filed: Oct. 8, 2015

(86) PCT No.: PCT/IN2015/050130
§ 371 (c)(1),
(2) Date: Apr. 10, 2017

(87) PCT Pub. No.: WO2016/056030
PCT Pub. Date: Apr. 14, 2016

(65) Prior Publication Data
US 2017/0298038 A1    Oct. 19, 2017

(30) Foreign Application Priority Data
Oct. 8, 2014  (IN) ........................... 2866/DEL/2014

(51) Int. Cl.
| | | |
|---|---|---|
| *C07D 307/33* | (2006.01) | |
| *B01J 23/46* | (2006.01) | |
| *B01J 37/03* | (2006.01) | |
| *B01J 37/02* | (2006.01) | |

(52) U.S. Cl.
CPC .......... *C07D 307/33* (2013.01); *B01J 23/462* (2013.01); *B01J 37/0201* (2013.01); *B01J 37/0236* (2013.01); *B01J 37/035* (2013.01)

(58) Field of Classification Search
CPC .................................................... C07D 307/33
USPC .......................................................... 549/326
See application file for complete search history.

(56) References Cited

FOREIGN PATENT DOCUMENTS

WO    WO 2010/151343 A1    12/2010

OTHER PUBLICATIONS

International Search Report and Written Opinion for PCT/IN2015/050130 dated Feb. 4, 2017, 4 pgs.
PCT Demand and Amendment under Article 34 for PCT/IN2015/050130 as filed on Aug. 8, 2016, 24 pgs.
Written Opinion of the International Preliminary Examining Authority for PCT/IN2015/050130 dated Sep. 21, 2016, 4 pgs.
International Preliminary Report on Patentability for PCT/IN2015/050130 dated Jan. 12, 2017, 19 pgs.
Ana Primo et al., "Synergy between the metal nanoparticles and the support for the hydrogenation of functionalized carboxylic acids to diols on Ru/TiO2," Chemical Communications—CHEMCOM, vol. 47, No. 12, Jan. 1, 2011, pp. 3613-3615, 3 pgs.
Ortiz-Cervantes Carmen et al., "Hydrogenation of levulinic acid to [gamma]-valerolactone using ruthenium nanoparticles," Inorganic Chimica Acta 397 (2013) 124-128, Elsevier by, NL, vol. 397, Dec. 7, 2012, 5 pgs.
P.G.J. Koopman et al., "Induction effects in liquid phase hydrogenation catalyzed by Ruthenium on Carbon," Colloids and Surfaces, No. 3, Jan. 1, 1981, pp. 1-12, 12 pgs.

*Primary Examiner* — Taofiq A Solola (57) ABSTRACT

The present invention discloses a fast and selective process for the preparation of γ-valerolactone (Gvl) by catalytic hydrogenation of biomass-derived levulinic acid (LA) using recyclable ruthenium (Ru)-based heterogeneous catalysts in aqueous medium in stoichiometric yields (~100%) under mild reaction conditions using nearly required amount of hydrogen.

14 Claims, 4 Drawing Sheets

Fig. 6A - $^1$H-NMR of synthesized Gvl     Fig. 6B - $^{13}$C-NMR of synthesized Gvl

PROCESS FOR THE PREPARATION OF GAMMA-VALEROLACTONE BY CATALYTIC HYDROGENATION OF LEVULINIC ACID USING RU-BASED CATALYSTS

This is a National Phase Application under 35 USC 371 of PCT/IN2015/050130 filed Oct. 8, 2015 (published on Apr. 14, 2016 as WO 2016/056030); which claims priority to Indian Application No. 2866/DEL/2014 filed Oct. 8, 2014; all of which are incorporated by reference herein in their entirety.

FIELD OF THE INVENTION

The present invention relates to a process for the preparation of γ-valerolactone (Gvl) by catalytic hydrogenation of levulinic acid (LA) using Ru-based catalysts. Particularly the present invention relates to preparation of γ-valerolactone (Gvl) by catalytic hydrogenation of biomass-derived levulinic acid (LA) and its esters using ruthenium-based heterogeneous catalysts. More particularly, the invention relates to preparation of γ-valerolactone under near ambient conditions in short reaction time with high yield. Furthermore, the active Ru-based heterogeneous catalysts are efficiently recyclable.

BACKGROUND AND PRIOR ART OF THE INVENTION

Depleting fossil resources spurred interest for sustainably producing polymers, chemicals and fuels indispensable for mankind. Biomass is the one of the viable and renewable alternatives in particular for the production of chemicals and polymers as it is the only renewable source that has carbon. In particular, plant biomass is the valuable feedstock for chemical industry as it contains oils, carbohydrates, lignin, proteins, waxes, and secondary metabolites. Nature produces large amounts of plant biomass through the process of photosynthesis, in which carbohydrates are most abundant. Carbohydrates derived oxygenated chemical platforms have the potential opportunity through diverse synthetic protocols in making energy and chemicals sustainably, necessary for the future generation.

Levulinic acid (LA) is one such building block platform chemical identified by the U.S. Department of Energy; it is prepared from sugars by dehydration followed by hydrolysis via intermediate, 5-hydroxymethylfurfural (HMF). LA is a precursor for the preparation of various value added products, among which γ-valerolactone (Gvl) is an important product obtained through selective hydrogenation. Many research groups after conducting several experiments, concluded that Gvl is a sustainable liquid, which can be used in the production of energy and carbon-based consumer products, as it is easy to handle and store (γ-valerolactone—A sustainable liquid for energy and carbon-based chemicals. *Green Chem.* (2008) 10, 238-242).

Figure 1:
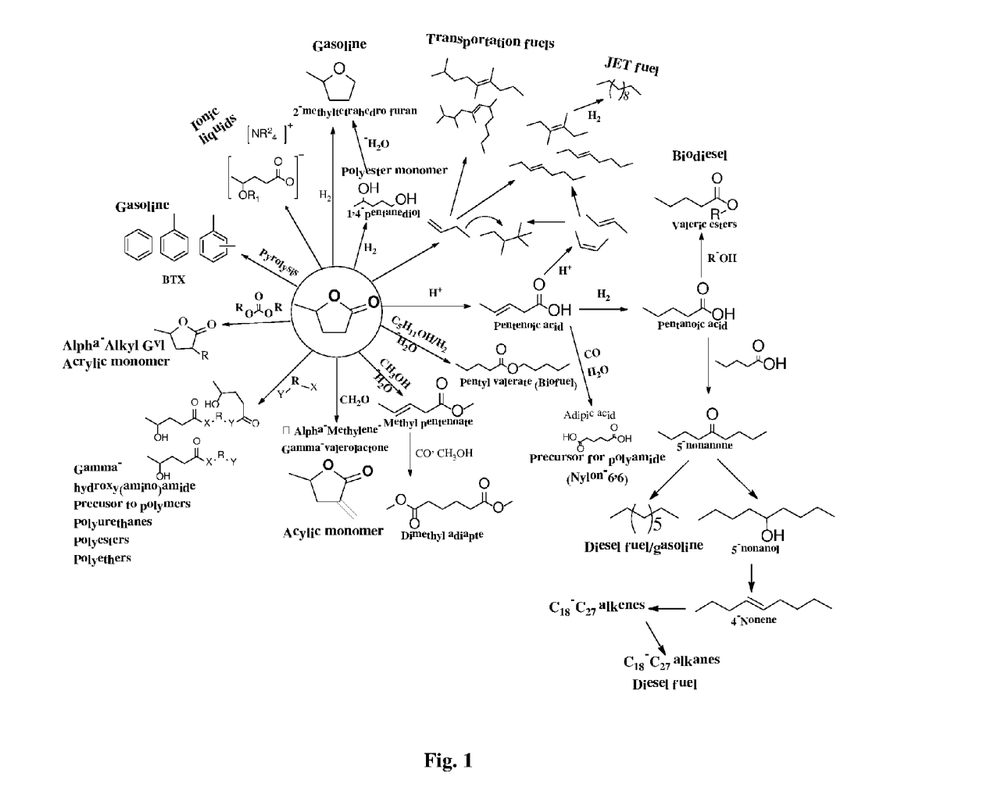
FIG. 1: Applications of Gvl in different industrial sectors

Catalytic hydrogenation of LA to Gvl is an important step in bio refinery because it has several industrial applications such as in biofuels (valeric and liquid alkanes for transportation fuels), additive in biofuel, and as eco-friendly high boiling solvent in particular for biomass conversions and in many organic transformations. In addition, Gvl is a raw material in the production of various chemicals (aromatic hydrocarbons and γ-hydroxy-amides), and polymers (nylon intermediates such as adipic acid, dimethyl adipate and caprolactam). The applications of Gvl are shown in FIG. 1.

Worldwide several research groups are working in developing an efficient conversion protocol for LA to Gvl through hydrogenation using various hydrogen sources like molecular hydrogen, formic acid, and alcohols. However, till date no catalytic process has been reported to be effective near ambient conditions and in shorter time with high yields. Details of some the efficient catalytic systems reported in the prior-art are discussed below.

W. Leitner's research group in their paper titled "Selective and flexible transformation of biomass derived platform chemicals by a multifunctional catalytic system" in *Angew. Chem. Int. Ed.* (2010) 49, 5510-5514 reported Ru (PnOct$_3$) as an active catalyst for LA conversion to Gvl at 160° C., 100 bar H$_2$ pressure in 18 h in presence of NH$_4$PF$_6$ as additive. Drawbacks of the work are high temperature, high pressure, long reaction time and necessity of additional chemicals. In addition, the complexes are homogeneous and hence not recyclable and poses separation and disposal problems.

L. T. Mika and his research group in their paper titled "Efficient catalytic hydrogenation of LA: A key step in biomass conversion" in *Green Chem.* (2012) 14, 2057-2065 reported 99.9% yield of Gvl using Ru (acac)$_3$ with bulky phosphine ligands as catalyst at 140° C., 10 bar H$_2$ pressure in 4.5 h. Drawbacks of the work are high temperature and longer reaction time. In addition, the catalyst is homogeneous and hence not recyclable. Moreover, it involves many synthetic steps and use expensive reagents for the preparation of catalyst.

F. E. Kuhn in his paper titled "Catalytic hydrogenation of LA in aqueous phase' in *Journal of Organometallic Chemistry* (2013) 724, 297-299 studied the reaction using various water soluble bulkier phosphine ligands along with Ru (acac)$_3$ as catalyst and achieved 99% of LA conversion with 97% selectivity of Gvl at 140° C., 50 bar H$_2$ in 5 h. The main drawbacks are multi-step synthesis of complexes and harsh reaction conditions.

Q-L Zhou et al., in Chinese Patent 102558108 have disclosed the use of iridium trihydride complexes as catalysts for the conversion of LA to Gvl in presence of base and solvent and achieved 96% of Gvl yield. Drawbacks of the work are synthesis of complexes that involves complex multi-step reaction that required controlled conditions, long reaction time (15 h), requirement of additional bases, and use of organic solvents. Further, the complexes are homogeneous and pose difficulties during separation.

To overcome the problems associated with homogeneous catalysts, heterogeneous catalysts were also used for this reaction.

L. E. Manzer in U.S. Pat. No. 6,617,464 B2 disclosed the preparation of Gvl from LA in presence of optionally supported metal catalysts which are preferably selected from the group consisting of Ir, Pd, Pt, Re, Rh, and Ru supported on various supports like carbon, silica and alumina, and the combination of metal and support thereof. He found that Ru on carbon as the more active catalyst at 140 to 160° C., pressure 55 bar H$_2$ in 2 h than other metal and/or supports. The drawbacks of the process are high reaction temperature, high pressure, and necessity of prior reduction of catalyst that require additional energy and raw material.

In another Chinese Patent 101733096 B, a process for the preparation of acid resistant catalysts is disclosed for effective hydrogenation of LA to Gvl. In this invention metal like Rh, Pt and Pd as catalysts were taken along with co-catalysts such as MnO$_2$, BaO, and ZrO$_2$ on carbon support. These catalysts showed good activity at 120 to 150° C., 10-100 bar H$_2$ for 1 to 8 h. The drawbacks of the process are requirement of additional energy and use of raw materials as co-catalysts, and harsher reaction conditions.

A. M. R. Galletti et al., in their paper titled "A sustainable process for the production of γ-valerolactone by hydrogenation of biomass-derived levulinic acid" in *Green Chem.* (2012) 14, 688 disclosed Ru/C catalysts with the combination of various heterogeneous acid co-catalyst and found that Amberlyst A70 as co-catalyst showed higher yield (99.5%) at 70° C., 5 bar $H_2$ within 3 h in aqueous medium. The drawbacks of the process are necessity of large amount of acid co-catalyst and long reaction time.

Y. Yang et al., in their paper titled "New route toward building active ruthenium nanoparticles on ordered mesoporous carbons with extremely high stability" in *Scientific Reports* (2014) 4, 4540 reported ruthenium nanoparticles on ordered mesoporous carbon as novel catalyst which showed high catalytic activity (99.4% LA conversion and 98.8% Gvl yield) at 150° C., 45 bar $H_2$ within 2 h. Although their catalyst has high recycling ability, the drawbacks of the work are higher reaction temperature, pressure, and energy intensive synthesis of mesoporous carbon support that needed many additional chemicals.

C. V. Rode et al., in U.S. Pat. No. 8,975,421 B2 have disclosed recyclable Cu—$ZrO_2$ nanocomposite as catalyst for maximum conversion of LA (100%) with 100% of Gvl selectivity at 200° C., 35 bar $H_2$ for 5 h. Although this process claimed the use of inexpensive non-precious metal catalyst, harsh reaction conditions employed to achieve high yield is the main drawback of this process.

Globally, many research groups and industries reported several catalytic systems for selective conversion of LA to Gvl using hydrogen. However, till now no catalyst is available in the prior art that would enable this reaction with high yields under mild conditions (near room temperature and to the extent of hydrogen necessary) in shorter time (in less than 60 minutes) without using additional raw materials such as co-catalysts, ligands, chemicals involved in the preparation of catalysts.

OBJECTIVES OF THE INVENTION

The main objective of the present invention is to provide a process for the preparation of γ-valerolactone (Gvl) by catalytic hydrogenation of levulinic acid (LA) or its esters using Ru-based catalysts Another object of the present invention is to provide an improved fast and selective process for the preparation of γ-valerolactone (Gvl) by catalytic hydrogenation of levulinic acid (LA) and its esters using Ru-based solid catalysts which obviates the drawbacks mentioned above.

Another object of the present invention is to use Ru-based catalysts having lesser amount of ruthenium with respect to LA.

Another object of the present invention is to selectively prepare Gvl at near room temperature.

Another object of the present invention is to use nearly stoichiometric quantity of hydrogen.

Still another object of the present invention is to prepare Gvl in shorter reaction time.

Another object of the present invention is to use catalysts without any prior reduction.

Yet another object of the present invention is to efficiently recycle the catalysts.

Still another object of the present invention is to demonstrate the process on larger scale to affirm industrial attractiveness.

SUMMARY OF THE INVENTION

Accordingly the present invention is to provide a process for the selective preparation of γ-valerolactone (Gvl) from levulinic acid (LA) and its esters in excellent yields (100%) using Ru-based catalysts. The process was performed in a solvent medium, preferably using water as solvent, at a temperature in the range of 25-200° C. and with a hydrogen pressure in the range of 3-50 bar, ruthenium loading in the range of 0.05-1 wt. % with respect to LA and the concentration of LA in the range of 1-50 wt. % with respect to solvent and for the reaction time of 2 min to 12 h.

In an embodiment of the present invention, an improved and fast process for the selective preparation of Gvl from biomass-derived LA and its esters using Ru-based catalysts in solvent medium was developed which comprises the following steps:

(i) mixing levulinic acid or its esters and solvent in a Hastealloy reactor vessel at a temperature in the range of 24 to 28° C. to form a solution;

(ii) adding catalyst to the solution obtained in step (i) to obtain a mixture and closing tightly the reactor vessel with the head assembly of the reactor;

(iii) purging $H_2$ into the mixture obtained in step (ii) at 1-2 bar for three times and adding $H_2$ in the reactor vessel to attain specified pressure;

(iv) heating the reactor vessel after attaining the specified pressure using an electric heater to desired temperature and stir the reaction mixture after attaining desired temperature at defined speed for specified time;

(v) cooling down the reactor vessel and release the unreacted $H_2$ and remove the vessel from the head assembly and separating the catalyst to get the product mixture;

(vi) separating Gvl from the product mixture obtained in step (v) by extractive separation using dichloromethane (DCM), removing DCM by rotary evaporation that can be reused and analysing the separated Gvl both qualitatively and quantitatively.

In another embodiment of the present invention, Ru-based catalysts used are Ru-supported zeolite (e.g., Ru/NaY), Ru-supported layered double hydroxides (e.g., Ru/MgAl-LDH; LDH-layered double hydroxide), hydrous ruthenium oxide (HRO) and its supported forms and $RuO_2$, preferably Ru/MgAl-LDH, HRO and its supported forms.

In yet another embodiment of the present invention, supports, including commercial supports, for loading HRO are selected from cellulose, $TiO_2$, Na-β zeolite, H-β zeolite, carbon, MCM-41, MgAl-LDH, preferable supports are Na-β, H-β and MCM-41.

In another embodiment of the present invention, the temperature of the reaction medium varied in the range 25° C. to 200° C., preferably 50 to 200° C. and more preferably 50 to 100° C.

In another embodiment of the present invention, the pressure of hydrogen varied in the range 3 to 50 bar, preferably in the range of 3-30 bar, more preferably in the range of 3-15 bar.

In another embodiment of the present invention, the amount of ruthenium in the catalyst used varied in the range 0.05 wt. % to 1 wt. % with respect to LA, preferably 0.1 wt. % to 0.5 wt. %.

In another embodiment of the present invention, LA concentration varied in the range 1 to 50 wt. %, preferably in the range of 2.5 to 25 wt. %.

In another embodiment of the present invention, the reaction time varied in the range 2 min to 12 h, preferably in the range 2 min. to 60 min., more preferably in the range 2 min. to 30 min.

In yet another embodiment of the present invention, solvents used to carry out the reaction are selected from methanol, ethanol and isopropanol, tetrahydrofuran, 1,4-dioxane, and water and mixtures thereof, preferably in water.

In still another embodiment of the present invention, the substrates used are levulinc acid (LA), and its esters such as methyl levulinate (MeL), ethyl levulinate (EtL) and butyl levulinate (BuL).

In another embodiment of the present invention, 100% conversion of LA with 100% yield of Gvl achieved using HRO and supported catalysts under mild conditions.

In yet another embodiment of the present invention, the preferred catalysts recycled with same activity.

In yet another embodiment of the present invention, the catalysts used are without any prior reduction and the active catalyst is generated via in situ reduction (to Ru(0)) under the reaction conditions.

ABBREVIATIONS

HRO: Hydrous ruthenium oxide
HRO-C: Hydrous ruthenium oxide prepared by precipitation method using $RuCl_3$ with $CaCO_3$
HRO-N: Hydrous ruthenium oxide prepared by precipitation method using $RuCl_3$ with NaOH
HRO-SA: Commercial hydrous ruthenium oxide sourced from M/s Sigma-Aldrich
1U-HRO-C: One time used HRO-C
2U-HRO-C/H-β: Twice used HRO-C supported on H-β

DETAILED DESCRIPTION OF THE INVENTION

The invention will now be described in detail in connection with certain preferred and optional embodiments, so that various aspects thereof may be more fully understood and appreciated.

The present invention discloses a fast, mild and selective process for the preparation of γ-valerolactone (Gvl) by catalytic hydrogenation of biomass-derived levulinic acid (LA) using recyclable Ru-based heterogeneous catalysts in aqueous medium with maximum yield of Gvl (100%) while operating under mild reaction conditions.

In the present invention selective hydrogenation of LA to Gvl is achieved in excellent yield (100%) under mild reaction conditions in short reaction time in aqueous medium using recyclable Ru-based heterogeneous catalysts, in particular, hydrous ruthenium oxide (HRO) or its supported forms that does not require prior reduction and with lesser amount of Ru (with respect to LA), using nearly stoichiometrically required amount of $H_2$. In comparison with the previous prior-art including those reported using Ru-based catalysts, the disclosed catalysts have improved activity, less energy demanding, conserving optimal utility of raw materials, needs shorter time and thus industrially more attractive.

The reactor was loaded with substrate (LA and LA esters), solvent, and catalysts at one time. The reaction was conducted at desired temperature and $H_2$ pressure for a specified period of time. After completion of the reaction, reactor was cooled to room temperature and unconsumed hydrogen was released. The solid catalyst was separated by centrifugation and used for next cycle without any treatment. The liquid product mixture was quantified using ultra high-performance liquid chromatography (UHPLC). In the absence of catalyst, no conversion of LA was noted at 20 bar $H_2$, 120° C. for 1 h and conversion of LA did not occur over HRO-C catalyst at 120° C. for 1 h in the absence of hydrogen. These two experiments showed that conversion of LA to Gvl requires both catalyst and $H_2$.

The catalysts used in the invention are hydrous ruthenium oxide (HRO-C, HRO-N and HRO-SA), supported HRO-C, $RuO_2$, Ru/MgAl-LDH and Ru/NaY. The HRO catalyst was prepared by using conventional precipitation method using NaOH or through a modified method using $CaCO_3$. In addition, a commercially available HRO catalyst was also purchased from M/s Sigma-Aldrich and used. $RuO_2$ catalyst was prepared by calcination of HRO-C in a muffle furnace at 550° C. for 3 h. Supported Ru catalysts (Ru/MgAl-LDH and Ru/NaY) were prepared by impregnation method using dilute $RuCl_3$ solution (0.001 M). Supported HRO-C catalysts (supports used are cellulose, $TiO_2$, Na-βzeolite, H-β zeolite, MCM-41, SBA-15, MgAl-LDH, and carbon) were prepared by precipitation followed by impregnation using dilute $RuCl_3$ solution (0.001 M) and $CaCO_3$ as precipitating agent.

Figure 2A:
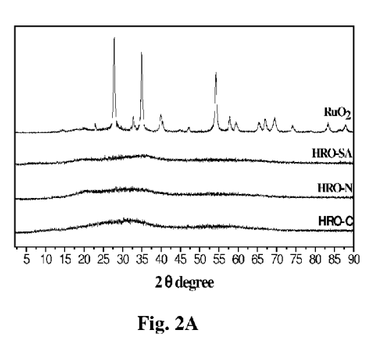
FIG. 2A: PXRD of HRO-C, HRO-N, HRO-SA and $RuO_2$
Figure 3A:
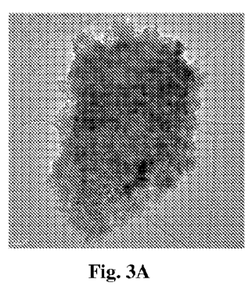
FIG. 3A: TEM image of HRO-C
Figure 3B:
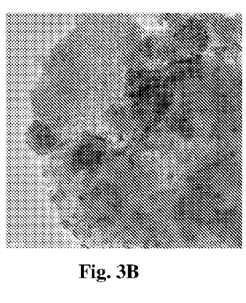
FIG. 3B: TEM image of HRO-C/H-β

The Ru-based catalysts used in this invention were characterized by using various analytical techniques in particular by using powder X-ray diffraction (PXRD), thermogravimetric analysis (TGA), Fourier-transformed infrared (FT-IR) spectroscopy, and transmission electron microscopy (TEM). The PXRD of HRO (HRO-C, HRO-N and HRO-SA) material did not show any diffraction peaks (FIG. 2A) suggests amorphous characteristic of this material. The TGA of HRO-C material showed weight loss in range of 150-350° C. (FIG. 4), attributed to weight loss of strongly adsorbed $H_2O$ molecules. The $H_2O$ molecules in HRO-C catalyst was also confirmed by FT-IR which showed broad band centred at 3440 $cm^{-1}$ (FIG. 5) ascribed to O—H stretching. The particles of Ru in HRO-C catalyst are agglomerated as observed by TEM (FIG. 3A) probably due to both bonding and non-bonding (hydrogen bonding) interactions through oxygen atoms.

The present invention provides hydrogenation of LA to Gvl using Ru-based catalysts in presence of solvent selected from water, alcohols (methanol, ethanol and isopropanol), tetrahydrofuran (THF), and 1,4-dioxane either alone or in combination thereof. The invention concludes water alone as an excellent medium for the reaction (eco-friendly medium) that provided 100% yield of Gvl under optimized conditions.

The reaction was performed at a temperature in the range of 25-200° C. and with a hydrogen pressure in the range of 3-50 bar, the ruthenium loading in the range of 0.05-1 wt. % with respect to LA, the concentration of LA is in the range of 1-50 wt. % with respect to solvent.

The reaction progress was monitored at different time intervals in the range of 2 min to 12 h. In particular, using HRO, HRO-C/H-β and Ru/MgAl-LDH as catalysts, the reactions were performed at temperature in the range of 25-200° C. and with a hydrogen pressure in the range of 3-10 bar, the ruthenium loading in the range of 0.1-0.5 wt. % with respect to LA, the concentration of LA is in the range of 1-25 wt. % with respect to solvent and the reactions were monitored in the time interval in the range of 2 min to 1 h.

Figure 6A:
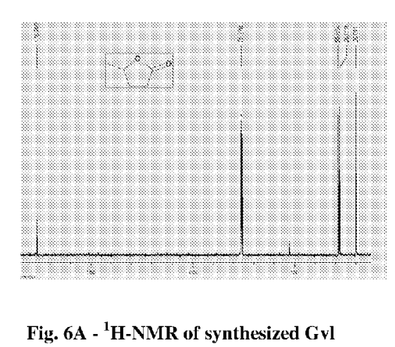
FIG. 6A: $^1$H-NMR spectra of synthesized Gvl using HRO-C/H-β catalyst
Figure 6B:
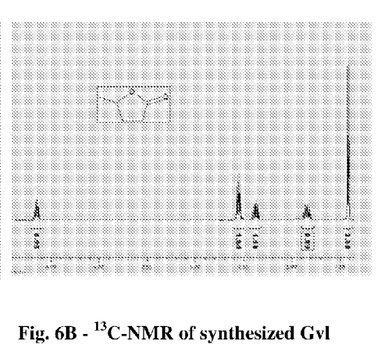
FIG. 6B: $^{13}$C-NMR spectra of synthesized Gvl using HRO-C/H-β catalyst
Figure 6C:
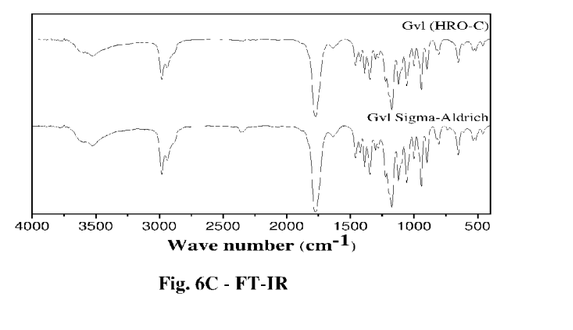
FIG. 6C: FT-IR spectra of synthesized Gvl using HRO-C/H-β catalyst with Gvl sourced from M/s Sigma-Aldrich.
Figure 6D:
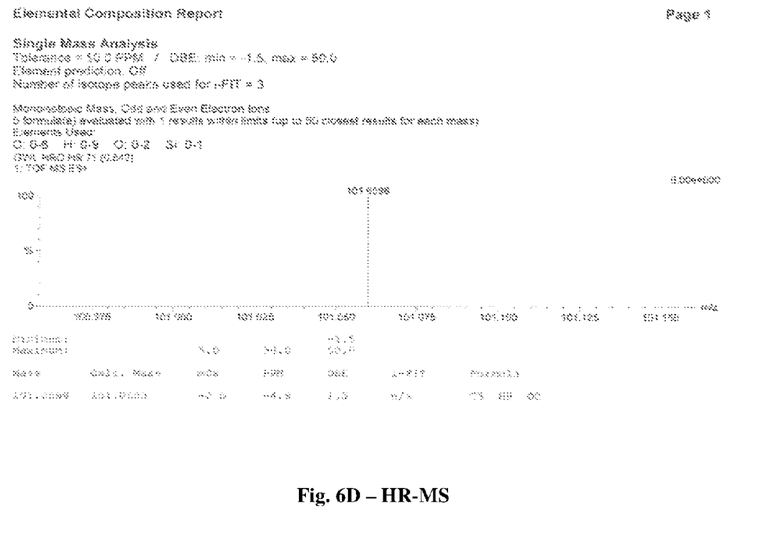
FIG. 6D: HR-MS of synthesized Gvl using HRO-C/H-β catalyst

100% conversion of LA with 100% yield of Gvl was achieved using HRO-C/H-β catalyst under mild reaction conditions viz., 50° C., 10 bar $H_2$ for 45 min. Stoichiometric yield was achieved over Ru/MgAl-LDH under optimized reaction conditions 80° C., 10 bar $H_2$ for 30 min. The invention provided quantitative and qualitative analysis of prepared Gvl wherein quantitative analysis was carried out by using UHPLC and the qualitative analysis was ascertained by using $^1$H NMR (FIG. 6A), $^{13}$C NMR (FIG. 6B), FT-IR (FIG. 6C) and HR-MS (FIG. 6D).

The selective preparation of Gvl was also observed in presence of HRO-C, supported HRO-C and Ru/MgAl-LDH catalyst using various levulinic esters namely methyl levulinate (MeL), ethyl levulinate (EtL) and butyl levulinate (BuL). The reactions were carried out under similar conditions that are used for LA. The hydrogenation of LA esters to Gvl were also carried out in presence of solvents selected from water, alcohols, THF, and 1,4-dioxane either alone or in combination thereof and preferably in water.

The active catalyst (HRO-C) was impregnated on different supports to widen the scope of the reaction window by varying parameters such as metal loading, temperature, pressure and time, besides easier recovery of the catalyst. Among the supports studied, the preferred supports for HRO-C with maximum dispersion are MCM-41, Na-β, and H-β, and more preferred support is Na-β or H-β (in terms of cost).

The active catalyst (HRO-C/H-β) was recycled and reused up to five reaction cycles without drop in its catalysts activity. The catalyst was recovered from the product mixture by simple centrifugation, the obtained solid was washed with water and dried at room temperature and used for the next cycle and the same procedure was repeated for five cycles and observed 100% yield of Gvl in all cases.

The catalytic activity of HRO-C was compared with other conventionally used catalysts such as $RuCl_3$ and 5% $Ru/Al_2O_3$ for this reaction. A set of the reactions were carried out at 100° C., 10 bar $H_2$, and using 0.35 wt. % of Ru metal (with respect to LA) for 15 min. The HRO-C catalyst showed better catalytic activity (100% yield of Gvl) than conventional catalysts $RuCl_3$ (10% LA conversion, 7% yield of Gvl) and 5% $Ru/Al_2O_3$ (30% LA conversion, 30% yield of Gvl).

In another comparison, the most conventionally used commercial hydrogenation catalyst namely 5% Ru/C (M/s Sigma-Aldrich) was tested. The reaction was carried out using 2.5 wt. of LA 1 (1 g of LA in 40 ml $H_2O$) using 50 mg of catalyst at 10 bar $H_2$ pressure and at 50° C. for 45 min. The yield of Gvl obtained was 39%. Under equivalent experimental conditions HRO-C/H-β showed 100%.

Increase in the wt. % of LA from 2.5 to 25 wt. % was studied for this reaction along with the extent of leaching of metal using inductively coupled plasma—optical emission spectrometry (ICP-OES). Negligible leaching was found up to 12.5 wt. % of LA while beyond which high leaching of metal (Ru) was observed.

The reaction was scaled up for 20 g using 12.5 wt. % LA in water that showed 100% yield of Gvl demonstrates the scalability of the process. The product mixture was extracted with dichloromethane (DCM) for three times and observed that, the entire Gvl was extracted into DCM from the aqueous reaction mixture. The DCM was rotary evaporated to separate Gvl and the collected DCM was reused for subsequent product mixture extraction. Using this extractive separation technique, a maximum recovery of Gvl was realized (>95%) which is more energy efficient than distilling out water from the aqueous product mixture. The purity of Gvl as ascertained through HR-MS (FIG. 6D) and UHPLC was better than 99%.

Figure 2B:
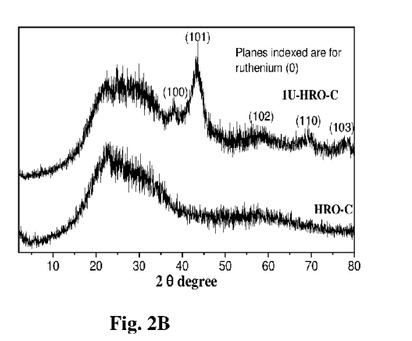
FIG. 2B: PXRD of a. HRO-C before reaction b. HRO-C after reaction (1U-HRO-C)
Figure 3C:
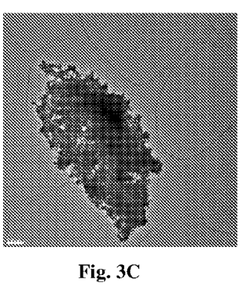
FIG. 3C: TEM image of 2U-HRO-C
Figure 4:
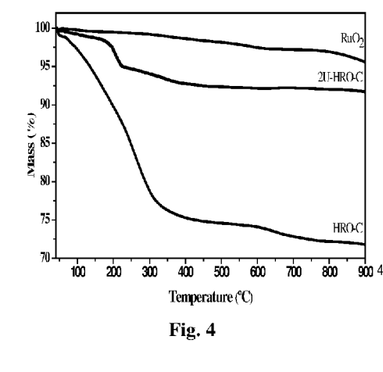
FIG. 4: TGA of catalysts (HRO-C, 2U-HRO-C and $RuO_2$)
Figure 5:
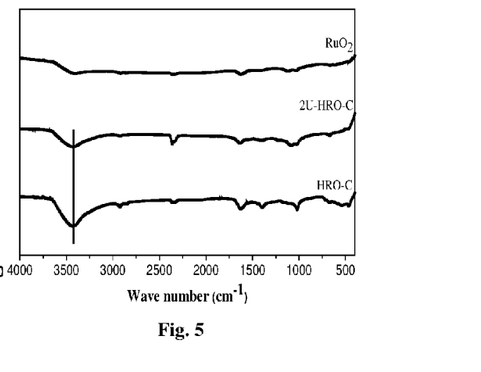
FIG. 5: FT-IR spectra of catalysts (HRO-C, 2U-HRO-C and $RuO_2$)

The HRO catalyst used in the reaction is as such without any prior reduction and identified the occurrence of in situ reduction during the reaction. The in situ reduction of HRO catalyst during the reaction was confirmed by various analytical techniques namely PXRD, TEM, FT-IR and TGA. HRO, being an amorphous material (+3 and +4 oxidation state) did not show any diffraction peaks in PXRD while after the reaction the material showed an intense peak at 43.7° (101 plane; FIG. 2B) that can be indexed to hexagonal closed-packed (hcp) structure of ruthenium(0) (JCPDS: 06-0663). However, the extent of agglomeration of Ru particles of HRO-C catalyst (after the reaction) showed a decrease as inferred from TEM suggest disintegration of Ru nanoparticles from aggregated HRO-C particles (FIG. 3C). The TGA of fresh HRO-C showed a weight loss up to 24% in the temperature 150 to 350° C. (removal of strongly held $H_2O$ molecules) while the loss observed for the used HRO-C catalyst (after $2^{nd}$ cycle) was 6% only (FIG. 4). This was also witnessed by FT-IR that showed a decrease in the intensity of O—H stretching band for the used HRO-C catalyst (FIG. 5). The catalyst Ru/MgAl-LDH and Ru/NaY have also underwent in situ reduction during the reaction.

We believe the invention preferred and claimed catalysts (HRO and Ru/Mg—Al LDH) have strongly adsorbed water molecules in their structure that are responsible for accessibility of LA molecules towards the active sites of the catalyst through hydrogen bonding and thus render high activity (*Chem. Commun.*, 2014, 50, 12450-12453).

EXAMPLES

Following examples are furnished to support the feasibility of the invention but not to limit the scope of the invention Catalysts Preparation

Example: 1

HRO—Hydrous ruthenium oxide (HRO) catalyst was prepared by both conventional precipitation method using NaOH (designated as HRO-N) and a modified precipitation method using $CaCO_3$ as precipitating agent (designated as HRO-C). For HRO-C, 500 ml 0.001M of $RuCl_3$ solution was added to $CaCO_3$ solution (100 mg in 2 L) and allowed to stand for 10 min with stirring at 25° C. The obtained precipitate was washed with water and dried at 100° C. for 6 h. The dried material was characterised by PXRD (FIG. 2A), FT-IR (FIG. 5) and TGA (FIG. 4). For HRO-N, to the stirred aqueous solution of ruthenium chloride ($RuCl_3.xH_2O$ M/s Sigma-Aldrich; 200 ml of 0.001 M) a solution of 0.3 M sodium hydroxide was added dropwise at 25° C. until pH=7 and thereafter stirred the mixture for 12 h. The obtained precipitate was washed with water and dried at 100° C. for 6 h. The PXRD of the obtained HROs (HRO-C and HRO-N) matched well with commercial M/s Sigma-Aldrich sample (HRO-SA; FIG. 2A).

Example: 2

Figure 2C:
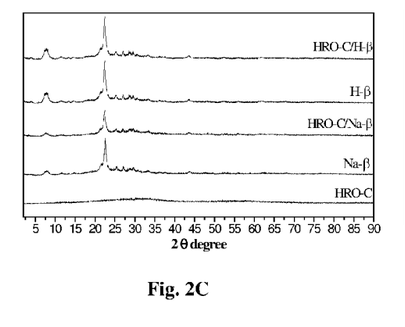
FIG. 2C: PXRD of HRO-C, Na-β, H-β, HRO-C/Na-β and HRO-C/H-β
Figure 2D:
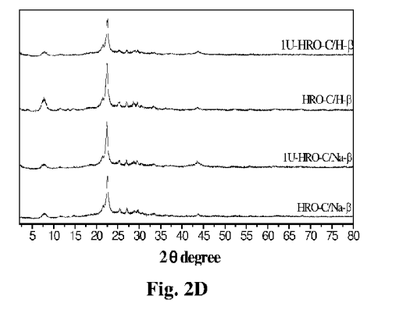
FIG. 2D: PXRD of a. HRO-C/Na-β before reaction b. HRO-C/Na-β after reaction (1U-HRO-C/Na-β) c. HRO-C/H-β before reaction d. HRO-C/H-β after reaction (1U-HRO-C/H-β).

HRO-C/H-β—HRO-C supported on H-β zeolite was prepared using precipitation followed by impregnation method. 500 ml solution of 0.001 M of $RuCl_3$ was added to precipitating agent which is 100 mg of $CaCO_3$ solution (2 L) and 1 g of commercial Na-β zeolite, and the resulting mixture was stirred for 12 h at 25° C. The obtained precipitate was washed with water and dried at 100° C. temperature for 6 h. The PXRD profile of the dried material is given in FIG. 2C.

Example: 3

$RuO_2$—20 mg of HRO-C (obtained from Example 1) was calcined at 550° C. for 3 h in a muffle furnace at a heating rate of 10° C./min. The solid obtained (15 mg) was $RuO_2$ as confirmed by PXRD by comparing with standard diffraction pattern (FIG. 2A).

Example: 4

Ru/MgAl-LDH or Ru/NaY—Ru supported MgAl-LDH (LDH-layered double hydroxide) and NaY catalysts were prepared by impregnation method. To 100 ml of 0.001 M $RuCl_3$ solution, 1 g of support material (MgAl-LDH and NaY) was added and stirred at 25° C. for 6 h. The solid obtained was collected by filtration and dried at 100° C. temperature for 6 h. The resulting material had 1 wt. % loading of Ru.

Catalytic Activity

Example: 5

1 g of LA was taken in 40 ml of $H_2O$ (2.5 wt. % of LA) in a 100 ml reactor vessel at temperature in the range of 24 to 28° C. To that, 3.5 mg of prepared HRO-C catalyst was added. The reactor vessel was pressurized with 5 bar $H_2$ and heated at 50° C. for 90 min. After completion of the reaction, the catalyst was separated by centrifugation and the obtained clear product mixture was analyzed by UHPLC. The yield of Gvl obtained was 100%.

Example: 6

1 g of LA was taken in 40 ml of $H_2O$ (2.5 wt. % of LA) in a 100 ml reactor vessel at 25° C. To that, 3.5 mg of prepared HRO-C catalyst was added. The reactor vessel was pressurized with 5 bar $H_2$ and heated at 25° C. for 12 h. After completion of the reaction, the catalyst was separated by centrifugation and the obtained clear product mixture was analyzed by UHPLC. The yield of Gvl obtained was 48%.

Example: 7

1 g of LA was taken in 40 ml of $H_2O$ (2.5 wt. % of LA) in a 100 ml reactor vessel at 27° C. To that, 3.5 mg of prepared HRO-C catalyst was added. The reactor vessel was pressurized with 5 bar $H_2$ and heated at 50° C. for 30 min. After completion of the reaction, the catalyst was separated by centrifugation and the obtained clear product mixture was analyzed by UHPLC. The yield of Gvl obtained was 40%.

Example: 8

1 g of LA was taken in 40 ml of $H_2O$ (2.5 wt. % of LA) in a 100 ml reactor vessel at 26° C. To that, 3.5 mg of prepared HRO-C catalyst was added. The reactor vessel was pressurized with 10 bar $H_2$ and heated at 100° C. for 15 min. After completion of the reaction, the catalyst was separated by centrifugation and the obtained clear product mixture was analyzed by UHPLC. The yield of Gvl obtained was 100%.

Example: 9

1 g of LA was taken in 40 ml of $H_2O$ (2.5 wt. % of LA) in a 100 ml reactor vessel at 28° C. To that, 3.5 mg of prepared HRO-N catalyst (prepared by NaOH precipitation method) was added. The reactor vessel was pressurized with 10 bar $H_2$ and heated at 100° C. for 15 min. After completion of the reaction, the catalyst was separated by centrifugation and the obtained clear product mixture was analyzed by UHPLC. The yield of Gvl obtained was 100%.

Example: 10

1 g of LA was taken in 40 ml of $H_2O$ (2.5 wt. % of LA) in a 100 ml reactor vessel at 25° C. To that, 3.5 mg of prepared HRO-SA catalyst was added. The reactor vessel was pressurized with 10 bar $H_2$ and heated at 100° C. temperature for 15 min. After completion of the reaction, the catalyst was separated by centrifugation and the obtained clear product mixture was analyzed by UHPLC. The yield of Gvl obtained was 100%.

Example: 11

1 g of LA was taken in 40 ml of $H_2O$ (2.5 wt. % of LA) in a 100 ml reactor vessel at 27° C. To that, 3.5 mg of prepared $RuO_2$ catalyst was added. The reactor vessel was pressurized with 10 bar $H_2$ and heated at 100° C. for 15 min. After completion of the reaction, the catalyst was separated by centrifugation and the obtained clear product mixture was analyzed by UHPLC. No yield of Gvl or conversion of LA was observed.

Example: 12

1 g of LA was taken in 40 ml of $H_2O$ (2.5 wt. % of LA) in a 100 ml reactor vessel at 28° C. To that, 50 mg of prepared HRO-C/H-β catalyst was added. The reactor vessel was pressurized with 10 bar $H_2$ and heated at 50° C. for 45 min. After completion of the reaction, the catalyst was separated by centrifugation and the obtained clear product mixture was analyzed by UHPLC. The yield of Gvl obtained was 100%.

Example: 13

1 g of LA was taken in 40 ml of $H_2O$ (2.5 wt. % of LA) in a 100 ml reactor vessel at 26° C. To that, 50 mg of prepared HRO-C/H-β catalyst was added. The reactor vessel was pressurized with 5 bar $H_2$ and heated at 100° C. for 10 min. After completion of the reaction, the catalyst was separated by centrifugation and the obtained clear product mixture was analyzed by UHPLC. The yield of Gvl obtained was 100%.

Example: 14

1 g of LA was taken in mixture of solvents (20 ml of $H_2O$ +20 g of methanol (2.5 wt. % of LA)) in a 100 ml reactor vessel at 27° C. To that, 50 mg of prepared HRO-C/H-β catalyst was added. The reactor vessel was pressurized with 10 bar $H_2$ and heated at 100° C. for 15 min. After completion of the reaction, the catalyst was separated by centrifugation and the obtained clear product mixture was analyzed by UHPLC. The yield of Gvl obtained was 0%.

Example: 15

1 g of LA was taken in 40 ml of $H_2O$ (2.5 wt. % of LA) in a 100 ml reactor vessel at 27° C. To that, 50 mg of prepared HRO-C/H-β catalyst was added. The reactor vessel was pressurized with 5 bar $H_2$ and heated at 150° C. for 4 min. After completion of the reaction, the catalyst was separated by centrifugation and the obtained clear product mixture was analyzed by UHPLC. The yield of Gvl obtained was 100%.

Example: 16

1 g of LA was taken in 40 ml of $H_2O$ (2.5 wt. % of LA) in a 100 ml reactor vessel at 26° C. To that, 50 mg of prepared HRO-C/H-β catalyst was added. The reactor vessel was pressurized with 5 bar $H_2$ and heated at 200° C. for 2 min. After completion of the reaction, the catalyst was separated by centrifugation and the obtained clear product mixture was analyzed by UHPLC. The yield of Gvl obtained was 100%.

Example: 17

1 g of LA was taken in 40 ml of $H_2O$ (2.5 wt. % of LA) in a 100 ml reactor vessel at 28° C. To that, 50 mg of prepared HRO-C/H-β catalyst was added. The reactor vessel was heated at 100° C. and pressurized with 3 bar $H_2$; after attaining pressure, the reaction mixture was stirred for 30 min. After completion of the reaction, the catalyst was separated by centrifugation and the obtained clear product mixture was analyzed by UHPLC. The yield of Gvl obtained was 100%.

Example: 18

1 g of methyl levulinate (MeL) was taken in 40 ml of $H_2O$ (2.5 wt. % of MeL) in a 100 ml reactor vessel at 27° C. To that, 3.5 mg of prepared HRO-C catalyst was added. The reactor vessel was pressurized with 10 bar $H_2$ and heated at 100° C. for 15 min. After completion of the reaction, the catalyst was separated by centrifugation and the obtained clear product mixture was analyzed by UHPLC. The yield of Gvl obtained was 50% with 100% conversion of MeL.

Example: 19

20 g of LA was taken in 160 ml of $H_2O$ (12.5 wt. % of LA) in a 300 ml reactor vessel at 28° C. To that, 1 g of prepared HRO-C/H-β catalyst was added. The reactor vessel was pressurized with 50 bar $H_2$ and heated at 150° C. for 30 min. After completion of the reaction, the catalyst was separated by centrifugation. The obtained product mixture was extracted with DCM for three times, and further evaporated by using rotary evaporator and obtained 17 g of Gvl with 100% of purity as inferred by using UHPLC. The purity of recovered Gvl was also ascertained by $^1H$ & $^{13}CNMR$, IR and HR-MS (FIG. 6A-6D).

Example: 20

1 g of LA was taken in 40 ml of $H_2O$ (2.5 wt. % of LA) in a 100 ml reactor vessel at 26° C. To that, 70 mg of prepared HRO-C/H-β catalyst was added. The reactor vessel was pressurized with 10 bar $H_2$ and heated at 100° C. temperature for 10 min. After the reaction the catalyst was separated by simple centrifugation and it was used as such for next cycle without any pre-treatment and this procedure was followed for five subsequent cycles. The catalyst activity did not change and all cycles gave 100% yield of Gvl.

Example: 21

1 g of LA was taken in 40 ml of $H_2O$ (2.5 wt. % of LA) in a 100 ml reactor vessel at 27° C. To that, 150 mg of prepared Ru/NaY catalyst was added. The reactor vessel was pressurized with 15 bar $H_2$ and heated at 120° C. for 4 h. After completion of the reaction, the catalyst was separated by centrifugation and the obtained clear product mixture was analyzed by UHPLC. The yield of Gvl obtained was 100%.

Example: 22

1 g of LA was taken in 40 ml of $H_2O$ (2.5 wt. % of LA) in a 100 ml reactor vessel at 27° C. To that, 150 mg of prepared Ru/MgAl-LDH catalyst was added. The reactor vessel was pressurized with 10 bar $H_2$ and heated at 80° C. temperature for 30 min. After completion of the reaction, the catalyst was separated by using centrifugation and the obtained clear product mixture was analyzed by UHPLC. The yield of Gvl obtained was 100%.

Example: 23

1 g of LA was taken in 40 ml of $H_2O$ (2.5 wt. % of LA) in a 100 ml reactor vessel at 26° C. To that, 150 mg of prepared Ru/MgAl-LDH catalyst was added. The reactor vessel was pressurized with 5 bar $H_2$ and heated at 120° C. for 1 h. After completion of the reaction, the catalyst was separated by centrifugation and the obtained clear product mixture was analyzed by UHPLC. The yield of Gvl obtained was 54% with 56% conversion of LA.

Advantages of the Invention

Reactions under mild conditions (50-100° C. and 5-15 atm. pressure of $H_2$)
Nearly 100% conversion of LA
Excellent selectivity for Gvl (100%)
Lesser reaction time (2-30 min)
Using lesser weight % of precious metal, here Ru, content
Reactions using heterogeneous catalysts
No necessity of prior reduction of the active catalyst and is in situ generated
Active catalyst is recyclable
Reactions in aqueous medium
Requirement of nearly stoichiometric quantity of hydrogen thereby avoiding recycle operations The active catalyst can be supported on inexpensive supports such as zeolites and LDHs for efficient recovery and reuse.

We claim:

1. A process for the preparation of γ-valerolactone (Gvl) by catalytic hydrogenation of levulinic acid (LA) and its esters using Ru-based heterogeneous catalysts without prior reduction chosen from the group consisting of Ru/NaY, Ru/MgAl-LDH, hydrous ruthenium oxide (HRO), and a supported form of HRO in a solvent at a temperature range in the range of 25 to 200° C. at pressure in the range of 3 to 50 bar comprising the following steps:
    (i) mixing levulinic acid or its esters with solvent in a Hastealloy® reactor vessel at a temperature in the range of 24 to 28° C. to form a solution;
    (ii) adding at least one of the Ru-based heterogeneous catalysts to the solution obtained in step (i) to obtain a mixture and purging $H_2$ into the mixture at 1-2 bar for three times after closing tightly the reactor vessel with the head assembly of the reactor;
    (iii) pressurizing the reactor vessel at the pressure in the range of 3 to 50 bar;
    (iv) heating the reactor vessel after attaining the specified pressure at a temperature ranging between 25 to 200° C. and stirring the reaction mixture after attaining the specified temperature for a period of time ranging between 2 min to 12 h;
    (v) cooling down the reactor vessel and release the unreacted $H_2$ and separating the catalyst to get the product mixture; and
    (vi) separating Gvl from the product mixture obtained in step (v) by extracting with dichloromethane (DCM) and removing DCM by rotary evaporation that can be reused.

2. The process as claimed in claim 1, wherein supports for HRO are selected from the group comprising cellulose, $TiO_2$, Na-β, H-β, MCM-41, SBA-15, MgAl-LDH, and carbon.

3. The process as claimed in claim 1, wherein the Ru content used with respect to LA is in the range of 0.05 wt. % to 1 wt. %.

4. The process as claimed in claim 1, wherein the LA concentration is in the range of 1 wt. % to 50 wt. %.

5. The process as claimed in claim 1, wherein the conversion of LA and yield of Gvl are in the range of 0% to 100%.

6. The process as claimed in claim 1, wherein the solvent is selected from water, methanol, ethanol and isopropanol, THF, and 1,4-dioxane either alone or in combination thereof.

7. The process as claimed in claim 1, wherein the LA is selected from methyl levulinate (MeL), ethyl levulinate (EtL) and butyl levulinate (BuL).

8. The process as claimed in claim 1, wherein the Ru-based heterogeneous catalysts are reusable with similar activity.

9. The process as claimed in claim 1, wherein the Ru content used with respect to LA is in the range of 0.1 wt. % to 0.5 wt. %.

10. The process as claimed in claim 1, wherein the Ru content used with respect to LA is 0.2 wt. %.

11. The process as claimed in claim 1, wherein the LA concentration is in the range of 2.5 wt. % to 25 wt. %.

12. The process as claimed in claim 1, wherein the LA concentration is 12.5 wt. %.

13. The process as claimed in claim 1, wherein the conversion of LA and yield of Gvl are in the range of 50% to 100%.

14. The process as claimed in claim 1, wherein the conversion of LA and yield of Gvl are 100%.

* * * * *